United States Patent [19]
Drach

[11] Patent Number: 4,643,716
[45] Date of Patent: Feb. 17, 1987

[54] MULTI-SIZE URETERAL STENT

[75] Inventor: George W. Drach, Tucson, Ariz.

[73] Assignee: The Kendall Company, Boston, Mass.

[21] Appl. No.: 863,668

[22] Filed: May 15, 1986

Related U.S. Application Data

[63] Continuation of Ser. No. 654,358, Sep. 26, 1984, abandoned.

[51] Int. Cl.$^4$ ............................................. A61M 25/00
[52] U.S. Cl. ......................................... 604/8; 604/281
[58] Field of Search .................. 604/8, 9, 164, 170, 604/280, 281; 128/127, 130

[56] References Cited

U.S. PATENT DOCUMENTS

| | | | |
|---|---|---|---|
| 3,680,562 | 8/1972 | Wittes et al. | 604/281 |
| 4,202,329 | 5/1980 | Korton | 128/130 |
| 4,212,304 | 7/1980 | Finney | 604/8 |
| 4,307,723 | 12/1981 | Finney | 604/8 |
| 4,405,314 | 9/1983 | Cope | 604/170 |
| 4,531,933 | 6/1985 | Noron et al. | 604/8 |
| 4,610,657 | 9/1986 | Denson | 604/8 |

*Primary Examiner*—John D. Yasko
*Attorney, Agent, or Firm*—Powell L. Sprunger

[57] ABSTRACT

A ureteral stent comprising, a catheter having a hollow elongated generally straight body portion, a retaining portion for retaining the catheter in the kidney of a patient adjacent a distal end of the body portion, and a proximal end portion extending proximally from the body portion, with the end portion being formed in a serpentine configuration which may be cut to length depending upon the length of the patient's ureter.

3 Claims, 2 Drawing Figures

MULTI-SIZE URETERAL STENT

This is a continuation of application Ser. No. 654,358, filed on Sept. 26, 1984, now abandoned.

BACKGROUND OF THE INVENTION

The present invention relates to ureteral stents.

In the past, ureteral stents for placement in the ureter of a patient have been known. Usually such stents have retaining means at both ends for retaining ends of the stent in the kidney and bladder. However, it has been necessary to have an inventory of various length stents, and then to match the various length stents to the requirements of the particular patient, which has resulted in inconvenience and added cost to the hospital.

SUMMARY OF THE INVENTION

A principal feature of the present invention is the provision of an improved ureteral stent.

The ureteral stent of the present invention comprises, a catheter having a hollow elongated generally straight body portion, means for retaining the catheter in the kidney of a patient adjacent a distal end of the body portion, and a proximal end portion extending proximally from the body portion, with the end portion being formed in a serpentine configuration.

A feature of the present invention is that the end portion may be cut to length depending upon the length of the patient's ureter.

Another feature of the present invention is that part of the cut end portion may be placed in the patient's ureter.

Yet another feature of the invention is that the cut end portion has one or more retaining loops in order to stabilize the catheter in the bladder.

Further features will become more fully apparent in the following description of the embodiments of this invention and from the appended claims.

DESCRIPTION OF THE PREFERRED EMBODIMENTS

Figure 1:
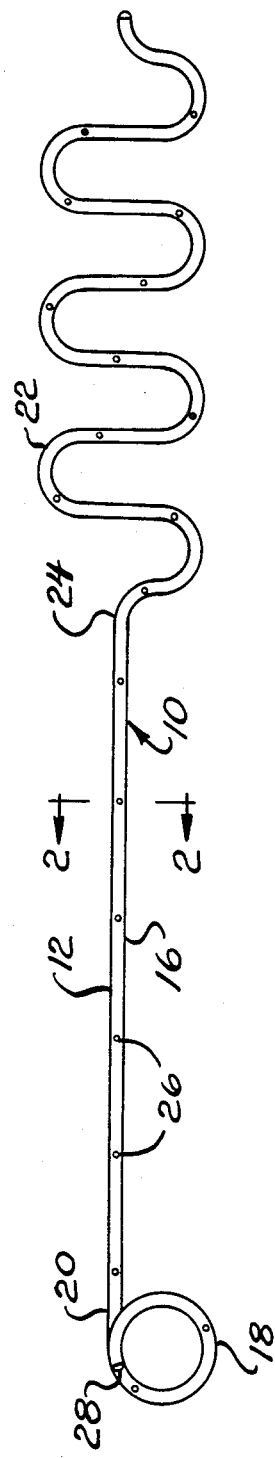
FIG. 1 is a plan view of a ureteral stent of the present invention.
Figure 2:
FIG. 2 is a sectional view taken substantially as indicated along the line 2—2 of FIG. 1.

Referring now to FIGS. 1 and 2, there is shown a ureteral stent generally designated 10 comprising a catheter 12 having a lumen 14 extending through the catheter 12. The catheter 12 has an elongated hollow straight central body portion 16, and a pig tail 18 extending from a distal end 20 of the body portion 16.

The catheter 12 has a proximal end portion 22 extending from a proximal end 24 of the body portion 16. As shown, the proximal end portion 22 is formed in a serpentine configuration such that it has a plurality of curlicues.

The catheter 12 has a plurality of apertures 26 along the length of the catheter 12 and extending between the outside of the catheter 12 and the lumen 14. The catheter 12 may have a closed distal end 28 in the pig tail 18, if desired. The catheter 12 may be constructed from any suitable elastic material, such as silicone.

In use, the catheter 12 is placed in the ureter through instrumentation or surgical intervention. The pig tail 18 is placed in the kidney of the patient in order to retain the distal portion of the catheter 12 in the patient. The proximal end portion 22 of the catheter 12 is cut to length depending upon the size of the patient's ureter. If necessary, a length of the end portion 22 may be straightened and placed in the ureter of the patient, and a sufficient length of the end portion 22 is allowed for providing one or more retaining loops of the end portion 22 for stabilization in the patient's bladder. After placement of the catheter 12, urine drains from the kidney and ureter through the apertures 26 into the lumen 14 for drainage into the patient's bladder.

The foregoing detailed description is given for clearness of understanding only, and no unnecessary limitations should be understood therefrom, as modifications will be obvious to those skilled in the art.

I claim:

1. A ureteral stent, comprising:
a catheter having a hollow elongated generally straight body portion, means for retaining the catheter in the kidney of a patient adjacent a distal end of the body portion, and a proximal end portion extending proximally from the body portion, said end portion being formed in a serpentine configuration disposed in a plane which may be cut to length depending upon the length of the patient's ureter, and a distal part of the remaining end portion may be straightened for alignment with the body portion and placement in the ureter while a part of the serpentine configuration proximal the straightened portion is maintained in the stent for placement in the bladder.

2. The stent of claim 1 wherein the retaining means comprises a pig tail.

3. The stent of claim 1 including a plurality of apertures disposed along the length of the catheter and extending through a wall of the catheter such that they communicate between a lumen in the catheter and the outside of the catheter.

* * * * *